Figure 1:
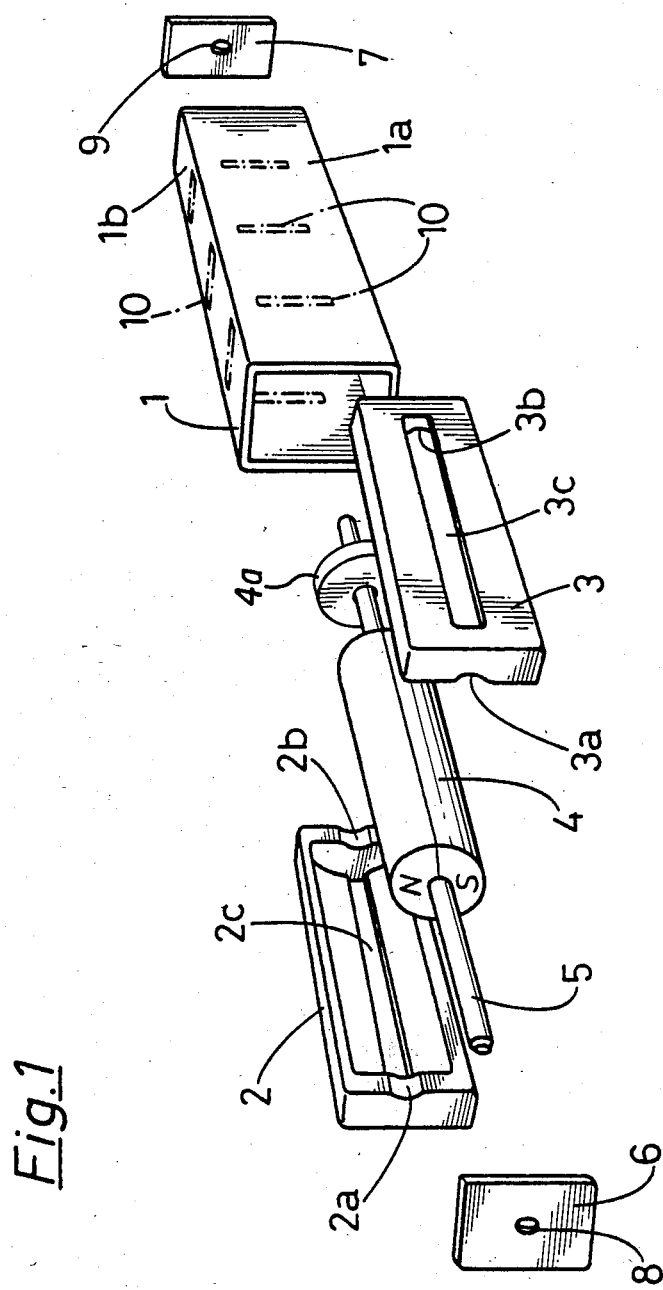

United States Patent [19]

Cuénoud

[11] Patent Number: 4,595,849
[45] Date of Patent: Jun. 17, 1986

[54] SMALL A.C. MOTOR HAVING AN OSCILLATORY PERMANENT MAGNET ARMATURE

[75] Inventor: Gérard Cuénoud, Grand Lancy, Switzerland

[73] Assignee: Les Produits Associes LPA SA, Switzerland

[21] Appl. No.: 744,642

[22] Filed: Jun. 13, 1985

Related U.S. Application Data

[63] Continuation of Ser. No. 420,298, Sep. 20, 1982, abandoned, which is a continuation-in-part of Ser. No. 243,902, Feb. 27, 1981, abandoned.

[30] Foreign Application Priority Data

Jul. 11, 1979 [CH] Switzerland .......................... 6449/79

[51] Int. Cl.$^4$ ............................................. H02K 33/00
[52] U.S. Cl. ........................................ 310/36; 310/38
[58] Field of Search ..................................... 310/36–39, 310/40, 42, 40 MM, 74, 29, 216

[56] References Cited

U.S. PATENT DOCUMENTS

| | | | |
|---|---|---|---|
| 1,136,942 | 4/1915 | Cutten | 310/42 X |
| 2,694,156 | 11/1954 | Cerminara | 310/29 |
| 2,890,357 | 6/1959 | Clark, Jr. | 310/40 X |
| 3,270,220 | 8/1966 | Isaacson | 310/40 |
| 3,471,725 | 10/1969 | Moret et al. | 310/36 |
| 3,475,629 | 10/1969 | Lagier | 310/36 |
| 3,512,022 | 5/1970 | Gilbert | 310/74 |
| 4,090,112 | 5/1978 | Selverstone | 310/36 X |

Primary Examiner—Donovan F. Duggan
Attorney, Agent, or Firm—Kane, Dalsimer, Kane, Sullivan & Kurucz

[57] ABSTRACT

The small a.c. motor which is intended in particular for the oscillating drive of a toothbrush fastened to the armature shaft, has as the armature a cylindrical permanent magnet (4) magnetized diametrically, a stationary coil surrounding this permanent magnet at a clearance along its whole length, its turns running essentially rectangularly, and a tubular stator case (1) surrounding the coil and of rectangular cross-section, to which the outer periphery of the coil being adapted. The coil is composed of two equal part-coils (2,3) and orientated with its axis perpendicular to the axis of the armature, and its planes of winding lie essentially in parallel with the large sidefaces of the stator (1). The two part-coils (2,3) rest against one another at faces orientated in parallel with their planes of winding in a plane passing through the armature axis, and their edges running diametrically to the armature have in the center semicircular recesses (2a,2b,3a,3b,) for the passage of the armature shaft (5).

Also on the armature there is a flywheel (4a) for adjusting the rotational inertia of the rota so that the natural frequency of the oscillation of the armature is lower than the supply frequency.

In modifications the stator case may also be square octagonal, or cylindrical, the outer periphery of the coil being adapted to the inner periphery of the stator. In case of a cylindrical stator radically projecting stator pole pieces may be provided, lying opposite one another on its periphery.

17 Claims, 11 Drawing Figures

SMALL A.C. MOTOR HAVING AN OSCILLATORY PERMANENT MAGNET ARMATURE

BACKGROUND OF THE INVENTION

This is a continuation to application Ser. No. 420,298, filed Sept. 20, 1982 now abandoned which is a continuation-in-part of application Ser. No. 243,902, filed on Feb. 27, 1981 now abandoned.

The invention refers to a small a.c. motor having an oscillating permanent magnet armature, in particular for the oscillating drive of a toothbrush attached to the armature shaft, with a cylindrical, diametrically magnetized permanent magnet as an armature and having a stationary coil.

Known a.c. motors of this kind (French Pat. No. 1 470-893) have rather complicated stator structures with several stator parts in double −T or Z form, where the bars on the inside form bent poles and surround the radially oriented middle parts of the stator.

In the case of know electric toothbrush (West German Pat. No. 1 119-819) the motor is supported in a caselike handle and exhibits an armature which oscillates at the frequency of the supply voltage and is fastened to a shaft onto which an interchangeable plug-on toothbrush can be mounted. Upon connection of the motor to the a.c. network, the plug-on toothbrush oscillates at he network frequency about the axis of the brush. The oscillating armature of this known a.c. motor is made in the form of a salient-pole rotor which has a permanent magnet having soft iron pole shoes and is held by a return spring in its rest position. The stator has two pole shanks forming poles and without windings, which are orientated in the direction longitudinal to the case and lie diametrically opposite one another; the pole shanks have arms prolonged beyond the region of the oscillating armature in the direction towards the rear end of the case, which are connected by a cross-yoke which carries the stator winding.

The object of the invention is to improve the motor efficiency as compared with know a.c. motors having oscillating armatures, in such a way that either approximately the same torque can be achieved at reduced power consumption or else a higher torque at approximately the same power consumption, and furthermore to design the construction of the motor in a particularly compact and simple way. The higher efficiency in particular allows the motor to operate at low voltage, that is, for example, at 20 V, which in the very case of electric toothbrushes or else massage appliances is particularly advantageous for reasons of safety. Such a hand appliance can then preferably be fed from the network via a transformer and as regards its electrical insulation does not need to fulfill any strict regulations.

The problem is solved according to the invention in that the coil is orientated with its magnetic axis perpendicular to the armature axis and surrounds the permanent magnet, where its turns run essentially rectangularly, and that the stator is a tubular part of the case, coaxial with the axis of the armature and of magnetizable material, which encloses the coil.

This produces a simple, space-saving structure and an optimal degree of efficiency because the armature consists of a simple cylindrical permanent magnet which is surrounded over its whole length by the stationary coil which in turn lies inside the tubular case of the stator. With this compact arrangement having an armature coaxial with the stator case and a coil lying between them, which preferably takes up almost all the vacant space inside the stator; of course with the exception of the clearance required for the armature, the stray losses are restricted to a minimum. In addition this makes optimal use of the space taken by the coil and the stator.

The coil may preferably be composed of two essentially equal part-coils the plane of contact of which passes through the axis of the armature and which may be connected in series or in parallel, depending upon the supply voltage employed.

In a preferred embodiment the stator has a rectangular cross-section having a long and short pair of sidefaces, where the long sidefaces form preferred poles and thereby a geometry having variable reluctance dependent upon the position of the armature, without special pole shoes or projecting poles of some other shape being provided. In this way it can be achieved that the torque exerted upon the armature by the magnetic field of the coils is strengthened by the static torque originating from the rectangular stator geometry, which tries to turn the armature so that the direction of magnetization of the permanent magnet is lying parallel with the short sideface of the stator. In order to make optimum use of this favorable effect, the magnetic axis of the coils must be orientated perpendicular to the long sidefaces of the stator and the armature in its rest position must be held by suitable return means, for example, by a return spring, in a position in which the direction of the diametrical magnetic field of the armature is lying perpendicular to the axis of the coil and thereby in parallel with the long sidefaces of the stator. Preferably the armature and the spring form a mechanical oscillatory system with a natural frequency which is equal to or lower than the frequency of the power supply. A similar effect is obtained by a stator with octogonol cross-section with a pair of opposite sidefaces which are larger than the other sidefaces. The same effect can also be achieved if a cylindrical stator case is chosen, having two projecting stator poles lying diametrically opposite one another on its inner periphery.

In the case of a particularly simple embodiment of the motor in accordance with this invention the stator consists merely of a cylindrical sleeve without projecting poles, whereby because of the symmetrical stator geometry no additional static torque acts upon the armature.

The invention will be described by way of example with reference to the drawings in which only electrical components necessary for an understanding of the invention are shown. There is shown in:

FIG. 1: a perspective view of a first embodiment having a rectangular stator case in an exploded arrangement of the individual parts.

Figure 2:
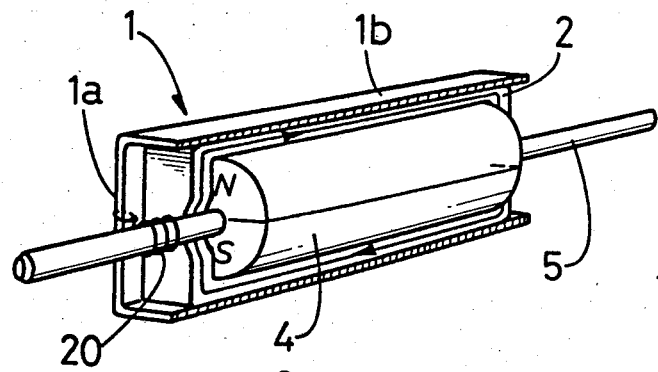

FIG. 2: the motor shown in FIG. 1 in an assembled state but with the stator shown cut open.

Figure 3:
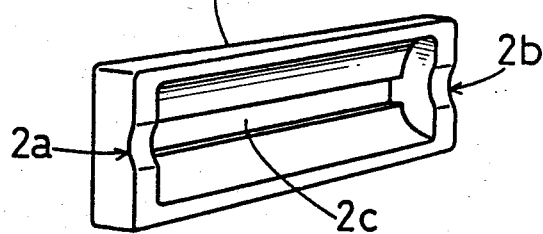
Figure 4:
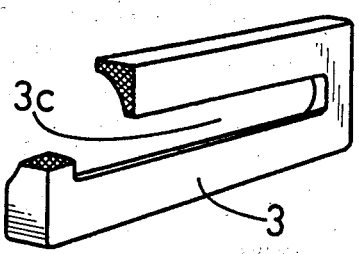
Figure 5:
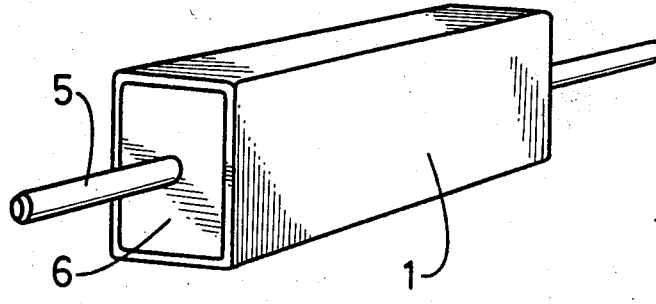
Figure 6:
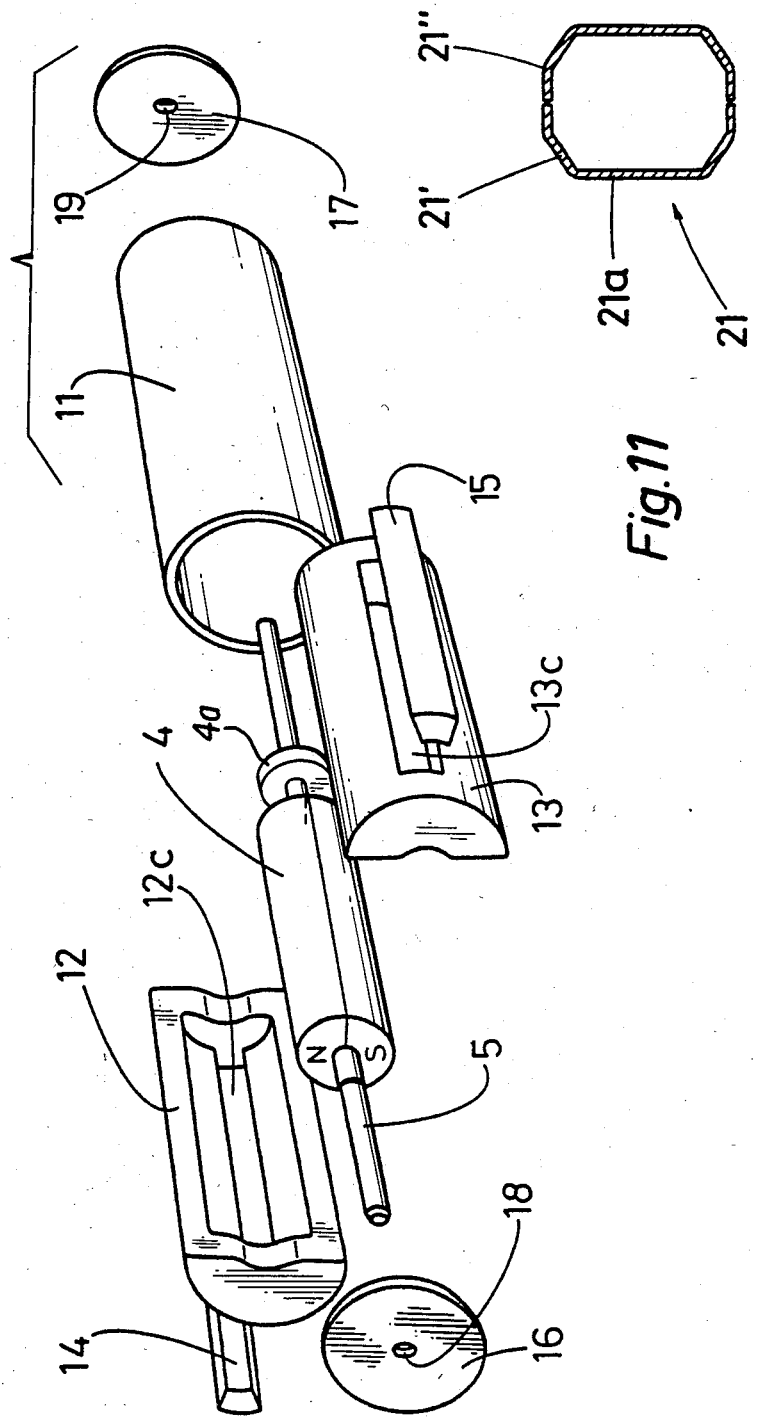

FIG. 3 a view of a one part coil,

FIG. 4: a view of the other part-coil in partial cross-section,

FIG. 5: an external view of the motor,

FIG. 6: a perspective view of a second embodiment having a cylindrical stator case in an exploded view.

Figure 7:
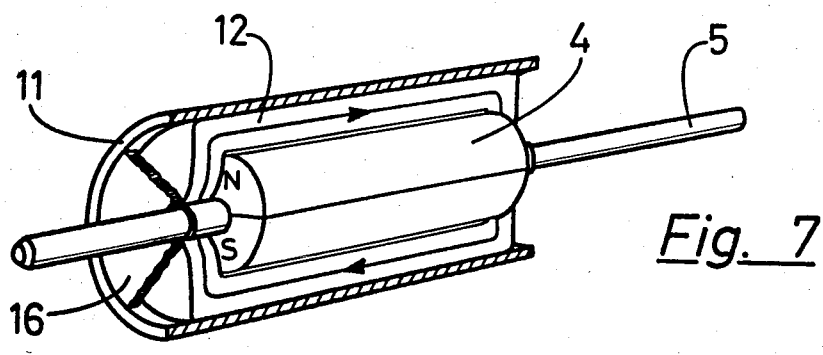

FIG. 7: the assembled motor shown in FIG. 6, but with the stator shown cut open.

Figure 8:
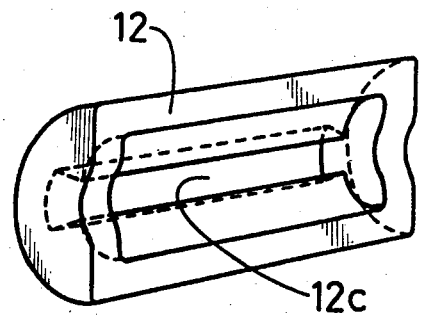
Figure 9:
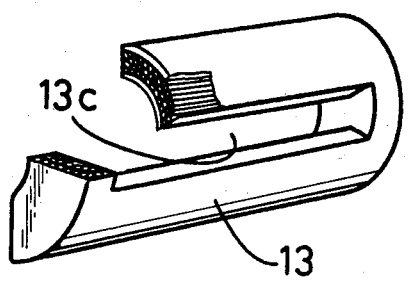
Figure 10:
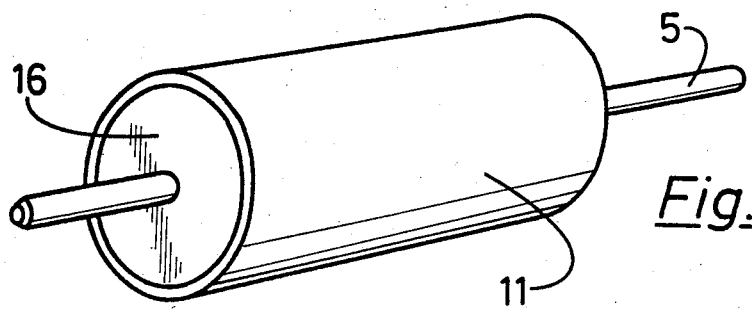

FIG. 8: a view of a one part-coil,

FIG. 9: a view of the other part-coil in partial cross-section,

FIG. 10: an external view of the motor, and

FIG. 11: a cross-section through an octogonal two-part stator of a third embodiment.

With reference to FIG. 1, the stator 1 of the a.c. motor consists of a tubular part of the case having a rectangular cross-section, which case is made of magnetizable material and has long or respectively large sidefaces 1a and the short or respectively small sidefaces 1b. The armature fastened to the armature shaft 5 consists of a cylindrical permanent magnet 4 having diametrical magnetization. The poles are indicated in FIG. 1 by the letters N and S. The armature shaft 5 may consists of magnetic material.

The permanent magnet 4 is surrounded over its whole length by a coil consisting of two part-coils 2 and 3, the sxis of which runs perpendicular to the armature shaft 5 and perpendicular to the long sidefaces 1a of the stator 1 and the direction of winding of which is indicated in FIG. 2 by arrows. The turns run essentially rectangularly and are adapted to the longitudinal cross-section of the cylindrical permanent magnet 4, passing through the axis. The part-coils 2 and 3 are constructed the same and rest against one another with their faces which point inwards and are orientated in parallel with their plane of winding, in a plane passing through the axis of the armature, the edges of the part-coil bodies; running diametrically to the armature, have in the centre approximately semi-circular recesses 2a, 2b, and 3a; and 3b, respectively, which is the assembled state complete openings for the armature shaft 5 to pass through. The outer periphery of the two part-coils 2 and 3 is adapted to the inner periphery of the rectangular stator 1, which in this way holds the coils essentially positively, so that the rectangular coil openings 2c, and 3c respectively lie in front of the long sidefaces 1a of the stator. The inner periphery of the part-coils 2 and 3 is adapted to the cylindrical shape of the permanent magnet 4. In this way the permanent magnet 4 is surrounded completely by the shell-like part-coils 2 and 3 with only slight clearance, whereby the vacant space between the armature and stator is in practice completely filled by the coil-turns. If necessary the coil arrangement can also be made in such a way that they only partially fill the vacant space within the stator.

Instead of two part-coils which facilitate the assembly of the motor, in principal only one part-coil may also be provided.

The end faces of the stator 1 are closed by two rectangular flanges 6 and 7 adapted to the cross-section of stator opening and exhibiting in the centre bearing openings 8 and 9 respectively for the armature shaft 5 to pass through, and may likewise consist of magnetic material.

On shaft there is also a flywheel 4a which is provided as a means of controlling the rotational inertia of the rotor. Thus, the natural frequency of oscillation of the motor may be adjusted in accordance with the supply frequency by installing an appropriate flywheel.

The motor described may typically have an axial length of about 55 mm, a height of about 20 mm and a width of about 15 mm. The power consumption in operation at 50 Hz or at 60 Hz may typically lie between 1.3 and 1.6 W.

For reduction of eddy current losses it may be advantageous to provide in the walls of the stator 1 as shown in broken lines in FIG. 1, slits 10 which run parallel with a plane orientated perpendicularly to the axis of the armature.

The motor described works as follow: the permanent magnet armature 4 in the rest position is forced by return means, for example, a return spring 20 surrounding the armature shaft 5 as indicated in FIG. 2, not a position which is shown in FIG. 2 and in which the direction of the diametrical magnetic field of the armature is lying perpendicular to the axis of the coil. If the part-coils 2 and 3, which may be connected in series or in parallel, depending upon the level of the supply voltage, are now energized by an alternating current, the alternating magnetic field H generated cooperates with the magnetic moment "m" of the armature magnet 4 in such a way that an alternating torque is exerted upon the armature of the value $$M = m.H \sin\alpha$$

where $\alpha$ is the angle between the direction of the magnetic field H and that of the armature magnetization and in the position of rest of the armature illustrated in FIG. 2 amounts to 90°. The armature thereby experiences an oscillating deflection out of its rest position, so that it oscillates at the frequency of the supply voltage.

In order to insure that the armature's deflection is at a maximum, the motor may be tuned so that the armature and the spring have a natural oscillation frequency fo which is slightly below the frequency of the supply voltage. Thus, for a 60 Hz supply, fo should be $53.5 \pm 3$ Hz, while for a 50 Hz supply fo should be $44 \pm 2.5$ Hz. The natural frequency of a mechanical oscillating system comprising a spring and a mass is given by $$fo = (\tfrac{1}{2}\pi)\sqrt{K/J}$$

where K is the affective spring constant and J is the moment of inertia.

The typical spring used in the motor has an actual spring constant of 0.124 Nxm/rad. However it has been found that the interaction due to the variable reluctance between the stator and the rotor reduces this value so that the effective spring constant has been found to be 0.0954 Nxm/rad. Since the spring constant is independent of frequency, the moment of inertia of the armature must be changed. From the above equations it is clear that the moment of inertia for the 60 Hz supply should be $0.844 \times 10^{-6}$ Kgxm$^2$ while for a 50 $-$Hz supply, J should be $1.25 \times 10^{-6}$ Kgxm$^2$. An easy way to accomplish this is to use the same armature 4 and change the size of the flywheel 4a. Thus for example, for an armature having $J = 0.53 \times 10^{-6}$ Kgxm$^2$ a flywheel having a moment of inertia of $0.314 \times 10^{-6}$ Kgxm$^2$ may be used at 60 Hz and a flywheel having a moment of inertia of $0.72 \times 10^{-6}$ Kgxm$^2$ may be used for 50 Hz.

The rectangular shape of the case of the stator now confers two additional advantageous effects. First this stator geometry for a given amount of copper in the wire of the coil allows the generation of a relatively high field in the direction axial to the coil. Secondly the magnetic circuit exhibits a reluctance which depends relatively strongly upon the angle between the axis of magnetization of the armature magnet 4 and the major axis of symmetry of the rectangular cross-section of the stator, since the two long or respectively large sidefaces 1a of the stator 1 have the function of preferred poles. The action of this variable reluctance consists of the following: When the armature is deflected a little out of its rest position shown in FIG. 2, which forms an unstable balance, in the absence of a coil field a static torque acts upon it, which tries to turn the armature into that position in which the reluctance of the magnetic circuit is least; in this position which differs from the rest position by an angle of 90°, the direction of magnetization of the armature magnet 4 is aligned with the minor axis of symmetry of the cross-section of the stator. This static torque advantageously strengthens the normal torque generated by the coil field and thereby favors the oscillating motion of the armature.

This effect of strengthening the useful torque may also be described by the statement that in the expression specified above for the torque "M" the value m, that is, the magnetic moment of the armature magnet, depends upon the aforesaid angle.

Under given electrical and magnetic conditions the value of the angle of oscillation of the armature depends upon the external loading and upon the tuning of the mechanical oscillating system, that is, upon the mass of the armature and the object fastened to it, upon the characteristic of the return means and upon the damping or friction respectively. Under certain circumstances this angle may amount to 180° and possibly even exceed this value. That is, if no measures are provided for limiting the angle of the armature and therefore the armature is free, the motor can behave as a rotating single-phase synchronous motor. But for the special application of the motor to the drive of a toothbrush the angle of oscillation of the armature and hence the oscillatory motion of the toothbrush about the axis of the brush is limited to an angle of about 60° or less.

The second embodiment of a motor in accordance with the invention in accordance with FIGS. 6 to 10 differs from the first embodiment in that the stator 11 consists of a cylindrical sleeve, that correspondingly the outer periphery of the coil which is again formed from two equal part-coils 12 and 13, in adaptation to the inner periphery of the stator is cylindrical and that the flanges 16 and 17 at the ends, which again exhibit bearing openings 18 and 19 for the armature shaft 5 to pass through, are circular in adaptation to the cross-section of the openings in the stator 11. The armature consists again as in the case of the first embodiment of as cylindrical permanent magnet 4 fastened onto the armature shaft and having diametrical magnetization. With the exception of the external contour of the coil the two part-coils 12 and 13 are constructed, orientated and arranged in the stator 11 exactly as in the case of the first embodiment.

In order to achieve the advantageous effect of additional static torque which, as explained with the aid of the first embodiment, originates in the case of the motor there described from the rectangular cross-section of the stator, in the case of the second embodiment as in FIG. 6 two separate stator pole pieces 14 and 15 of magnetizable material are provided, which lie diametrically opposite one another and rest against the inner periphery of the stator 11 or respectively are fastened to it. According to FIG. 6 these two stator pole pieces 14 and 15 have the shape of segments of a hollow cylinder and are adapted to the contour of the openings 12c and 13c respectively in the part-coils 12 and 13 respectively so that in the assembled state of the motor they engage in these openings in the coil. These two stator poles 14 and 15, projecting radially inwards, which may also be made in any other way or fastened or moulded onto the inner periphery of the stator, bring about in practice the same effect of a static torque as has been described with the aid of the first embodiment and has the result that the armature magnet 4 as soon as it is deflected a little out of its rest position shown in FIG. 7 experiences a torque which tries to turn it by 90° out of its rest position and which is superimposed upon the torque generated by the coil field. Besides this effect of a variable reluctance the projecting stator poles bring about a strengthening of the coil field.

By waiving the aforesaid effect of a static torque an a.c. motor in accordance with the invention may also exhibit a stator which consists only of a cylindrical case 11 (FIG. 6) and exhibits no projecting stator poles. This construction of a motor is particularly simple and has the advantage of a neutral balance as regards the rotation of the armature.

FIG. 11 shows the stator 21 with octogonal cross-section of a further embodiment of a motor in accordance with the invention, in the case of which, analogous to the example given in FIG. 1, the outer peripheries of the two halves of the coil not shown, are adapted to the octogonal internal periphery of the stator and advantageously take up practically all the vacant space between stator and armature. In order to facilitate production and assembly of the motor, in the example given in FIG. 11, two equal box-like halves of the stator 21' and 22' are provided, which are joined in a plane which at least approximately passes through the longitudinal axis of the stator 21 and are fixed together in any manner at all, which can be, for example, with the aid of flanges adapted to the octogonol cross-section, which, like the flanges as in FIG. 1, form the end faces of the stator. The two opposite side faces 21a of the stator 21 are larger than the other sidefaces, so that equal advantageous effects are produced, as explained for the rectangular stator 1 shown in FIG. 1 with its pair of long sidefaces orientated perpendicular to the large sidefaces 21a may generally be between 10 and 50%, preferably about 30% greater than the distance between the large sideface 21b. This applies also to the measurement of the rectangular stator shown in FIG. 1.

An octogonal form of stator as in FIG. 11 brings with it the additional advantages that the motor can be particularly well and space-saving accomodated in the grip-type casing with oval cross-section, such as used typically for electric toothbrushes, and that the maximum radial distance between armature and stator-sleeve is reduced by comparison with the diagonal dimensions in the case of a rectangular stator; in this way the volume of air or copper within the magnetic circuit is reduced and thus the field is enlarged. In addition, by amplifying the static torque a more favorable characteristic curve of the torque as a function of the armature angle is obtained.

Of course, also in the examples as shown in FIG. 1 and 6, the stator 1 and 11 respectively can be composed of two halves, analogous to the stator 21 according to FIG. 11.

The preferred application of the a.c. motor in accordance with the invention is the building into the handle-like case of an electric toothbrush having interchangeable plug-on toothbrushes; because of the relatively low power consumption such an electric toothbrush can then be supplied at low voltage via a transformer form the network, so that in practice no problems arise of electrical insulation. But the motor in accordance with the invention is also suitable for other purposes, for example, for massage appliances and for any application in the technical fields in which rapid periodic motion plays a part such, for example, as in small pumps.

The invention is not restricted to the embodiments described but as regards the construction and assembly of the individual parts, especially as regards the cross-section of the stator, which may also be oval, square, or generally polygonal, and as regards the coils, allows of manifold variants.

What is claimed is:

1. A small a.c. motor energized from a.c. supply and having an oscillating permanent magnet armature, in particular for the oscillating drive of a hand held appliance attached to the armature shaft, with a cylindrical diametrically magnetized permanent magnet as an armature and having a stationary coil, characterized in that the coil is orientated with its magnetic axis perpendicular to the longitudinal axis of the armature and surrounds the permanent magnet where its turns run essentially rectangularly, and that the stator is a tubular part of the case, coaxial with the axis of the armature and of magnetizable material, which encloses the coil; said armature having a rest position which is determined by a spring motion, said armature and spring forming an oscillatory system having a natural oscillatory frequency which is slightly lower than the a.c. supply frequency.

2. The small a.c. motor according to claim 1, characterized in that the coil comprises two at least approximately equal part-coils which rest against one another at faces orientated essentially parallel with their plane of wind in a plane passing at least approximately through the axis of the armature, the edges of the part-coils running approximately diametrically to the armature having at their centre semicircular recesses for the passage of the armature shaft.

3. The small a.c. motor according to claim 2, characterized in that the part-coils are connected in series or in parrallel depending upon the level of the supply voltage.

4. The small a.c. motor according to claim 3 characterized in that the tubular stator has a polygonal cross-section, in particular a square, rectangular or octogonal cross-section, whereby the axis of the coil preferably is orientated in parallel with one pair of opposite sidefaces of the stator.

5. The small a.c. motor according to claim 4, characterized in that the stator has a rectangular or octogonal cross-section in which the sidefaces of one pair of opposed sidefaces are larger than the other sides and form preferred poles, the axis of the coil being orientated perpendicular to the large sidefaces.

6. The small a.c. motor according to claim 5, characterized in that the distance between sidefaces of the stator orientated perpendicular to the larger sidefaces is between 10% and 50% preferably by about 30% larger than the distance between the larger sidefaces.

7. The small a.c. according to claim 3 motor characterized in that the tubular stator (11) is cylindrical.

8. The small a.c. motor according to claim 7, characterized in that the cylindrical stator has stator poles projecting diametrically opposite one another from its inner periphery, the line connecting the poles is orientated at least approximately in parrellel with the coil axis.

9. The small a.c. motor according to claim 8, characterized in that the stator poles are separate members each in the form of segments of a hollow cylinder, and which members engage in essentially rectangular lateral openings of the coil or respectively part-coils.

10. The small a.c. motor according to claim 9 characterized in that the outer periphery of the coil or respectively part-coils is adapted to the shape of the inner periphery of the stator and the winding turns take up approximately all the vacant space between armature and stator.

11. The small a.c. motor according to claim 9 characterized in that the two endfaces of the tubular stator are closed by flanges the shape of which is adapted to the cross-sectional shape of the stator and which define bearing openings for the armature shaft.

12. The small a.c. motor according to claim 1 characterized in that the tubular part of the case of the stator is provided with slits for the reduction of eddy currents which slits are arranged to run in parallel with a plane orientated perpendicular to the axis of the armature.

13. The small a.c. according to claim 12 motor characterized in that the tubular stator is composed of two box-like halves which rest against each other in a plane which passes at least approximately through the longitudinal axis of the stator.

14. The small a.c. motor according to claim 1 wherein said natural frequency is 53.5±3 Hz for a 60 Hz a.c. supply and 44±2.5 Hz for a 50 Hz a.c. supply.

15. The small a.c. motor according to claim 14 wherein said spring means has a spring constant of 0.0954 Nxm/rad and said armature has a moment of inertia of $0.844 \times 10^{-6}$ Kgxm$^2$ for a 60 Hz supply and $1.25 \times 10^{-6}$ Kgxm$^2$ for a 50 Hz supply 16. The small a.c. motor according to claim 15 wherein said armature comprises a permanent magnet having a moment of inertia of $0.53 \times 10^{-6}$ Kgxm$^2$ and a flywheel.

17. The small a.c. motor according to claim 16 wherein said flywheel has a moment of inertia of $0.314 \times 10^{-6}$ Kgxm$^2$ for a 60 Hz a.c. supply and $0.72 \times 10^{-6}$ Kgxm$^2$ for a 50 Hz a.c. supply.

* * * * *